(12) United States Patent
Quincy, III

(10) Patent No.: US 8,168,852 B2
(45) Date of Patent: May 1, 2012

(54) ACTIVATED CARBON SUBSTRATES

(75) Inventor: Roger Bradshaw Quincy, III, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 882 days.

(21) Appl. No.: 11/021,547

(22) Filed: Dec. 23, 2004

(65) Prior Publication Data

US 2006/0142709 A1   Jun. 29, 2006

(51) Int. Cl.
*A61F 13/53* (2006.01)
*B32B 5/30* (2006.01)

(52) U.S. Cl. ......................... 604/359; 428/207
(58) Field of Classification Search .................... 604/359
See application file for complete search history.

(56) References Cited

U.S. PATENT DOCUMENTS

| | | | |
|---|---|---|---|
| 2,408,418 A * | 10/1946 | Erickson et. al. | 127/46.1 |
| 2,593,146 A | 4/1952 | Howard | |
| 2,690,415 A * | 9/1954 | Shuler | 604/359 |
| 3,091,550 A * | 5/1963 | Doying | 427/387 |
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,616,797 A * | 11/1971 | Champaigne, Jr. et al. | 604/364 |
| 3,692,618 A | 9/1972 | Dorschner et al. | |
| 3,802,817 A | 4/1974 | Matsuki et al. | |
| 3,836,633 A | 9/1974 | Beschke | |
| 3,849,241 A | 11/1974 | Butin et al. | |
| 3,872,013 A * | 3/1975 | Nishino et al. | 210/317 |
| 4,100,324 A | 7/1978 | Anderson et al. | |
| 4,285,343 A | 8/1981 | McNair | |
| 4,297,233 A | 10/1981 | Gualandi | |
| 4,340,563 A | 7/1982 | Appel et al. | |
| 4,407,960 A | 10/1983 | Tratnyek | |
| 4,517,308 A | 5/1985 | Ehlenz et al. | |
| 4,608,047 A | 8/1986 | Mattingly | |
| 4,687,478 A | 8/1987 | Van Tilburg | |
| 4,753,728 A * | 6/1988 | VanderBilt et al. | 210/282 |
| 4,770,806 A * | 9/1988 | Sullivan et al. | 252/182.17 |
| 4,775,585 A | 10/1988 | Hagiwara et al. | |
| 4,802,473 A | 2/1989 | Hubbard et al. | |
| 4,950,264 A | 8/1990 | Osborn, III | |

(Continued)

FOREIGN PATENT DOCUMENTS

EP    0282287 B2    9/1988

(Continued)

OTHER PUBLICATIONS

The Merck Index, Budavari, Susan, et al., 1996, Merck & Co., Inc., 12th Edition, p. 831.*

(Continued)

*Primary Examiner* — Melanie Hand
*Assistant Examiner* — Paula Craig
(74) *Attorney, Agent, or Firm* — Dority & Manning, P.A.

(57) ABSTRACT

A substrate that contains an odor control composition is provided. The odor control composition includes activated carbon for adsorbing one or more odorous compounds to reduce odor. The odor control composition also contains a water-soluble binder for increasing the durability of the activated carbon when applied to a substrate. In addition to improving durability, such a water-soluble binder may also provide good drapability and low residual odor in the resulting coated substrate.

34 Claims, 1 Drawing Sheet

U.S. PATENT DOCUMENTS

| | | | |
|---|---|---|---|
| 4,969,457 A | | 11/1990 | Hubbard et al. |
| 5,009,653 A | | 4/1991 | Osborn, III |
| 5,020,533 A | | 6/1991 | Hubbard et al. |
| 5,085,654 A | | 2/1992 | Buell |
| 5,108,739 A | | 4/1992 | Kurihara et al. |
| 5,122,418 A | | 6/1992 | Nakane et al. |
| 5,183,656 A | | 2/1993 | Uesaka et al. |
| 5,190,563 A | | 3/1993 | Herron et al. |
| 5,197,959 A | | 3/1993 | Buell |
| 5,207,830 A | * | 5/1993 | Cowan et al. ............... 106/672 |
| 5,267,992 A | | 12/1993 | Van Tilburg |
| 5,284,703 A | | 2/1994 | Everhart et al. |
| 5,306,487 A | * | 4/1994 | Karapasha et al. .......... 424/76.6 |
| 5,308,346 A | | 5/1994 | Sneller et al. |
| 5,322,061 A | | 6/1994 | Brunson |
| 5,342,342 A | | 8/1994 | Kitaoka |
| 5,350,624 A | | 9/1994 | Georger et al. |
| 5,382,400 A | | 1/1995 | Pike et al. |
| 5,383,450 A | | 1/1995 | Hubbard et al. |
| 5,397,625 A | * | 3/1995 | Osteen et al. ................... 442/35 |
| 5,407,442 A | | 4/1995 | Karapasha |
| 5,429,628 A | | 7/1995 | Trinh et al. |
| 5,509,914 A | | 4/1996 | Osborn, III |
| 5,540,916 A | * | 7/1996 | Parks ............................ 424/76.1 |
| 5,553,608 A | | 9/1996 | Reese et al. |
| 5,569,234 A | | 10/1996 | Buell et al. |
| 5,634,916 A | | 6/1997 | Lavon et al. |
| 5,649,916 A | | 7/1997 | DiPalma et al. |
| 5,662,624 A | | 9/1997 | Sundström et al. |
| 5,681,299 A | * | 10/1997 | Brown ........................... 604/364 |
| 5,693,385 A | | 12/1997 | Parks |
| 5,702,378 A | | 12/1997 | Widlund et al. |
| 5,716,349 A | | 2/1998 | Taylor et al. |
| 5,733,272 A | | 3/1998 | Brunner et al. |
| 5,770,528 A | | 6/1998 | Mumick et al. |
| 5,813,398 A | | 9/1998 | Baird et al. |
| 5,834,114 A | | 11/1998 | Economy et al. |
| 5,851,651 A | * | 12/1998 | Chao ............................. 428/327 |
| 5,861,144 A | | 1/1999 | Peterson et al. |
| 5,874,067 A | | 2/1999 | Lucas et al. |
| 5,948,398 A | | 9/1999 | Hanamoto et al. |
| 6,096,299 A | | 8/2000 | Guarracino et al. |
| 6,110,158 A | | 8/2000 | Kielpikowski |
| 6,203,810 B1 | | 3/2001 | Alemany et al. |
| 6,344,218 B1 | | 2/2002 | Dodd et al. |
| 6,358,537 B1 | | 3/2002 | Hoshino et al. |
| 6,427,693 B1 | | 8/2002 | Blackstock et al. |
| 6,429,261 B1 | * | 8/2002 | Lang et al. .................... 525/191 |
| 6,436,128 B1 | | 8/2002 | Usui |
| 6,444,214 B1 | * | 9/2002 | Cole et al. ..................... 424/401 |
| 6,479,150 B1 | | 11/2002 | Liu et al. |
| 6,517,906 B1 | | 2/2003 | Economy et al. |
| 6,573,212 B2 | | 6/2003 | McCrae et al. |
| 6,576,810 B1 | | 6/2003 | Underhill et al. |
| 6,639,004 B2 | | 10/2003 | Falat et al. |
| 6,639,119 B2 | | 10/2003 | Roe et al. |
| 6,663,611 B2 | | 12/2003 | Blaney et al. |
| 6,680,289 B1 | | 1/2004 | Woo et al. |
| 6,740,406 B2 | | 5/2004 | Hu et al. |
| 2002/0161420 A1 | | 10/2002 | Usui |
| 2004/0043688 A1 | | 3/2004 | Soerens et al. |
| 2004/0063603 A1 | | 4/2004 | Dave et al. |
| 2004/0121681 A1 | | 6/2004 | Lindsay et al. |
| 2004/0121688 A1 | | 6/2004 | Edens et al. |
| 2004/0122387 A1 | | 6/2004 | Long et al. |
| 2004/0166248 A1 | | 8/2004 | Hu et al. |
| 2004/0176736 A1 | | 9/2004 | Christon et al. |
| 2004/0178384 A1 | | 9/2004 | Usui |
| 2004/0186214 A1 | * | 9/2004 | Li et al. ......................... 524/474 |
| 2005/0008776 A1 | * | 1/2005 | Chhabra et al. ............... 427/180 |
| 2005/0098495 A1 | * | 5/2005 | Hughes ...................... 210/502.1 |
| 2005/0131363 A1 | * | 6/2005 | MacDonald et al. .......... 604/367 |
| 2006/0137568 A1 | * | 6/2006 | MacDonald et al. ...... 106/31.13 |

FOREIGN PATENT DOCUMENTS

| | | |
|---|---|---|
| EP | 0348978 A2 | 1/1990 |
| EP | 0389015 A2 | 9/1990 |
| EP | 0427475 A1 | 5/1991 |
| EP | 0510619 A1 | 10/1992 |
| EP | 0749295 B1 | 12/1996 |
| EP | 0856302 A1 | 8/1998 |
| EP | 1034800 A1 | 9/2000 |
| EP | 1188854 A1 | 3/2002 |
| WO | WO 9112029 A1 | 8/1991 |
| WO | WO 9112030 A1 | 8/1991 |
| WO | WO 9820915 A1 | 5/1998 |
| WO | WO 9826808 A2 | 6/1998 |
| WO | WO 9826808 A3 | 6/1998 |
| WO | WO 9829079 A1 | 7/1998 |
| WO | WO 9900093 A1 | 1/1999 |
| WO | WO 9912734 A1 | 3/1999 |
| WO | WO 0103619 A1 | 1/2001 |
| WO | WO 02055115 A1 | 7/2002 |
| WO | WO 02059404 A2 | 8/2002 |
| WO | WO 02094329 A1 | 11/2002 |
| WO | WO 2004108589 A2 | 12/2004 |
| WO | WO 2004108589 A3 | 12/2004 |

OTHER PUBLICATIONS

Abstract of Japanese Patent No. JP03195562, Aug. 27, 1991.

Abstract of Japanese Patent No. JP03221142, Sep. 30, 1991.

Article—*Adsorption of Gases in Multimolecular Layers*, Stephen Brunauer, P. H. Emmett, and Edward Teller, The Journal of the American Chemical Society, vol. 60, Feb. 1938, pp. 309-319.

Fish, et al., U.S. Appl. No. 10/687,425, filed Oct. 16, 2003, Odor Absorbing Extrudates.

MacDonald, et al., U.S. Appl. No. 10/687,269, filed Oct. 16, 2003, Odor Controlling Article Including a Visual Indicating Device for Monitoring Odor Absorption.

Quincy, III et al., U.S. Appl. No. 10/723,761, filed Nov. 26, 2003, Odor Control in Personal Care Products.

Quincy, III et al., U.S. Appl. No. 10/749,689, filed Dec. 31, 2003, Odor Control Materials and Face Masks Including Odor Control Materials.

MacDonald et al., U.S. Appl. No. 10/955,316, filed Sep. 30, 2004, Odor-Reducing Quinone Compounds.

MacDonald et al., U.S. Appl. No. 11/021,485, filed Dec. 23, 2004, Patterned Application of Activated Carbon Ink.

MacDonald et al., U.S. Appl. No. 11/021,571, filed Dec. 23, 2004, Odor Control Substrates.

Abstract of Japanese Patent No. JP04255767, Sep. 10, 1992.

Abstract of Japanese Patent No. JP05098185, Apr. 20, 1993.

Product Data Bulletin on Nuchar® SA-20 from MeadWestvaco Corporation, 2002, 1 page.

Product Data Bulletin on Nuchar® SA-1500 from MeadWestvaco Corporation, 2002, 1 page.

Search Report and Written Opinion for PCT/US2005/035496, Apr. 13, 2006.

Abstract of Japanese Patent No. JP2004143232, May 20, 2004.

Written Opinion and Search Report for PCT/US2005/034363, May 4, 2006.

Written Opinion and Search Report for PCT/US2005/035499, May 8, 2006.

* cited by examiner

ACTIVATED CARBON SUBSTRATES

BACKGROUND OF THE INVENTION

Odor control additives have been conventionally incorporated into substrates for a variety of reasons. For instance, absorbent articles may contain odor control additives to absorb compounds that result in the production of malodors contained in absorbed fluids or their degradation products. Examples of these compounds include fatty acids, ammonia, amines, sulfur-containing compounds, ketones and aldehydes. Various types of odor control additives have been employed for this purpose. For instance, activated carbon has been used to reduce a broad spectrum of odors. In spite of its excellent properties as an adsorbent, the use of activated carbon in disposable absorbent articles has been limited by its black color. Activated carbon granules may also make unwanted noise or provide an undesirable gritty feel when incorporated into an article worn against the body. In addition, many conventional techniques for forming activated carbon substrate are simply too complex and/or costly for consumer applications.

As such, a need currently exists for activated carbon substrates that have good physical properties and are capable of reducing odor. Further, a need also exists for an improved method of making such activated carbon substrates.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

SUMMARY OF THE INVENTION

Figure 1:
FIG. 1 illustrates a plan view of a substrate that may be formed according to one embodiment of the present invention.

In accordance with one embodiment of the present invention, a substrate is disclosed that contains an odor control coating. The odor control coating comprises activated carbon, a binder, and a masking agent. The binder comprises a water-soluble organic polymer and the masking agent comprises masking particles. The masking particles have an average size that is less than the average size of the activated carbon. The resulting coating may reduce odor, and may also be more aesthetically appealing than conventional activated carbon substrates.

In accordance with another embodiment, a substrate is disclosed that contains an odor control coating. The odor control coating comprises activated carbon in an amount from about 1 wt. % to about 50 wt. %, a binder in an amount less than about 40 wt. %, and inorganic masking particles in an amount from about 20 wt. % to about 80 wt. %. The binder comprises a nonionic cellulosic ether and the inorganic particles have an average size of less than about 35 micrometers.

In accordance with still another embodiment of the present invention, a substrate is disclosed that contains an odor control coating. The odor control coating comprises activated carbon in an amount from about 1 wt. % to about 50 wt. %, a binder in an amount less than about 40 wt. %, and calcium carbonate particles in an amount from about 20 wt. % to about 80 wt. %. The binder comprises a nonionic cellulosic ether and the calcium carbonate particles have an average size of less than about 20 micrometers.

Other features and aspects of the present invention are described in more detail below.

DETAILED DESCRIPTION OF REPRESENTATIVE EMBODIMENTS

Definitions

As used herein, an "absorbent article" refers to any article capable of absorbing water or other fluids. Examples of some absorbent articles include, but are not limited to, personal care absorbent articles, such as diapers, training pants, absorbent underpants, adult incontinence products, feminine hygiene products (e.g., sanitary napkins), swim wear, baby wipes, and so forth; medical absorbent articles, such as garments, fenestration materials, underpads, bandages, absorbent drapes, and medical wipes; food service wipers; clothing articles; and so forth. Materials and processes suitable for forming such absorbent articles are well known to those skilled in the art.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, bonded carded web processes, etc.

As used herein, the term "meltblowing" refers to a process in which fibers are formed by extruding a molten thermoplastic material through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that may be continuous or discontinuous, are generally smaller than 10 microns in diameter, and are generally tacky when deposited onto a collecting surface.

As used herein, the term "spunbonding" refers to a process in which small diameter substantially continuous fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spun-bonded nonwoven webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are incorporated herein in their entirety by reference thereto for all purposes. Spunbond fibers are generally not tacky when they are deposited onto a collecting surface. Spunbond fibers may sometimes have diameters less than about 40 microns, and are often between about 5 to about 20 microns.

As used herein, the term "coform" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference thereto for all purposes.

As used herein, the "water vapor transmission rate" (WVTR) generally refers to the rate at which water vapor permeates through a material as measured in units of grams per meter squared per 24 hours ($g/m^2/24$ hrs). The test used to determine the WVTR of a material may vary based on the nature of the material. For instance, in some embodiments, WVTR may be determined in general accordance with ASTM Standard E-96E-80. This test may be particularly well suited for materials thought to have a WVTR of up to about 3,000 $g/m^2/24$ hrs. Another technique for measuring WVTR involves the use of a PERMATRAN-W 100K water vapor permeation analysis system, which is commercially available from Modern Controls, Inc. of Minneapolis, Minn. Such a system may be particularly well suited for materials thought to have a WVTR of greater than about 3,000 $g/m^2/24$ hrs. However, as is well known in the art, other systems and techniques for measuring WVTR may also be utilized.

As used herein, the term "breathable" means pervious to water vapor and gases, but impermeable to liquid water. For instance, "breathable barriers" and "breathable films" allow water vapor to pass therethrough, but are substantially impervious to liquid water. The "breathability" of a material is measured in terms of water vapor transmission rate (WVTR), with higher values representing a more vapor-pervious material and lower values representing a less vapor-pervious material. For example, even after being coated with an odor control coating, the "breathable" materials may have a water vapor transmission rate (WVTR) of from about 500 to about 20,000 grams per square meter per 24 hours ($g/m^2/24$ hours), in some embodiments from about 2,000 to about 15,000 $g/m^2/24$ hours, and in some embodiments, from about 5,000 to about 14,000 $g/m^2/24$ hours.

DETAILED DESCRIPTION

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

In general, the present invention is directed to a substrate that is coated with an odor control coating. The odor control coating contains activated carbon for adsorbing one or more odorous compounds to reduce odor, and also contains a water-soluble binder and masking particles. The use of a water-soluble binder may enhance the durability of the composition on the substrate, even when the composition is applied at high solid add-on levels. Further, the water-soluble binder may also provide good drapability and reduced residual odor for the resulting substrate. The masking particles may serve as a masking agent to alter or mask the black color associated with conventional activated carbon substrates, and also enhance the odor control properties of the substrate.

Generally speaking, activated carbon may be formed from a variety of sources, such as from sawdust, wood, charcoal, peat, lignite, bituminous coal, coconut shells, etc. Some suitable forms of activated carbon and techniques for formation thereof are described in U.S. Pat. No. 5,693,385 to Parks; U.S. Pat. No. 5,834,114 to Economy, et al.; U.S. Pat. No. 6,517,906 to Economy, et al.; U.S. Pat. No. 6,573,212 to McCrae, et al., as well as U.S. Patent Application Publication Nos. 2002/0141961 to Falat, et al. and 2004/0166248 to Hu, et al., all of which are incorporated herein in their entirety by reference thereto for all purposes. Regardless, the concentration of activated carbon is generally tailored to facilitate odor control without adversely affecting other properties of the substrate. For instance, activated carbon may be present in the coating (prior to drying) in an amount from about 1 wt. % to about 50 wt. %, in some embodiments from about 2 wt. % to about 30 wt. %, and in some embodiments, from about 5 wt. % to about 20 wt. %.

The odor control coating also contains a binder for increasing the durability of the coating to the substrate, even when present at high levels. The binder may also serve as an adhesive for bonding one substrate to another substrate. In addition to improving durability, the present inventor has also discovered that certain types of binders may provide properties to the resulting coated substrate. For instance, water-soluble organic polymers may be used as a binder in the present invention to improve drapability and residual odor. In addition, such water-soluble organic polymers may also provide a more aesthetically coating than other types of binders. One suitable class of water-soluble organic polymers includes polysaccharides and derivatives thereof. Polysaccharides are polymers containing repeated carbohydrate units, which may be cationic, anionic, nonionic, and/or amphoteric. In one particular embodiment, the polysaccharide is a nonionic, cationic, anionic, and/or amphoteric cellulosic ether. Suitable nonionic cellulosic ethers may include, but are not limited to, alkyl cellulose ethers, such as methyl cellulose and ethyl cellulose; hydroxyalkyl cellulose ethers, such as hydroxyethyl cellulose, hydroxypropyl cellulose, hydroxypropyl hydroxybutyl cellulose, hydroxyethyl hydroxypropyl cellulose, hydroxyethyl hydroxybutyl cellulose and hydroxyethyl hydroxypropyl hydroxybutyl cellulose; alkyl hydroxyalkyl cellulose ethers, such as methyl hydroxyethyl cellulose, methyl hydroxypropyl cellulose, ethyl hydroxyethyl cellulose, ethyl hydroxypropyl cellulose, methyl ethyl hydroxyethyl cellulose and methyl ethyl hydroxypropyl cellulose; and so forth.

Suitable cellulosic ethers may include, for instance, those available from Akzo Nobel of Stamford, Conn. under the name "BERMOCOLL." Still other suitable cellulosic ethers are those available from Shin-Etsu Chemical Co., Ltd. of Tokyo, Japan under the name "METOLOSE", including METOLOSE Type SM (methycellulose), METOLOSE Type SH (hydroxypropylmethyl cellulose), and METOLOSE Type SE (hydroxyethylmethyl cellulose). One particular example of a suitable nonionic cellulosic ether is ethyl hydroxyethyl cellulose having a degree of ethyl substitution (DS) of 0.8 to 1.3 and a molar substitution (MS) of hydroxyethyl of 1.9 to 2.9. The degree of ethyl substitution represents the average number of hydroxyl groups present on each anhydroglucose unit that have been reacted, which may vary between 0 and 3.

The molar substitution represents the average number of hydroxethyl groups that have reacted with each anhydroglucose unit. One such cellulosic ether is BERMOCOLL E 230FQ, which is an ethyl hydroxyethyl cellulose commercially available from Akzo Nobel. Other suitable cellulosic ethers are also available from Hercules, Inc. of Wilmington, Del. under the name "CULMINAL."

Another benefit of the water-soluble binder of the present invention is that it may facilitate the controlled release of the odor control coating from the substrate in an aqueous environment. Specifically, upon contacting an aqueous solution, the water-soluble binder dissolves and loses some of its binding qualities, thereby allowing other components of the odor control coating to be released from the substrate. This may be useful in various applications, such as for hard-surface wipers in which it is desired for the odor control components to be released into the wiped environment for sustained odor control. In other cases, however, it may be desired that the odor control coating remain adhered to the substrate, such as when the substrate is employed in certain types of absorbent articles. In such embodiments, it may be desired to employ a water-insoluble co-binder that does not substantially dissolve in an aqueous environment. Consequently, even upon dissolution of the water-soluble binder, the co-binder may help keep the components of the odor control coating adhered to the substrate. Suitable co-binders may include, for instance, those that become insoluble in water upon crosslinking. Crosslinking may be achieved in a variety of ways, including by reaction of the binder with a polyfunctional crosslinking agent. Examples of such crosslinking agents include, but are not limited to, dimethylol urea melamine-formaldehyde, urea-formaldehyde, polyamide epichlorohydrin, etc.

In some embodiments, a polymer latex may be employed as the co-binder. The polymer suitable for use in the lattices typically has a glass transition temperature of about 30° C. or less so that the flexibility of the resulting substrate is not substantially restricted. Moreover, the polymer also typically has a glass transition temperature of about −25° C. or more to minimize the tackiness of the polymer latex. For instance, in some embodiments, the polymer has a glass transition temperature from about −15° C. to about 15° C., and in some embodiments, from about −10° C. to about 0° C. For instance, some suitable polymer lattices that may be utilized in the present invention may be based on polymers such as, but are not limited to, styrene-butadiene copolymers, polyvinyl acetate homopolymers, vinyl-acetate ethylene copolymers, vinyl-acetate acrylic copolymers, ethylene-vinyl chloride copolymers, ethylene-vinyl chloride-vinyl acetate terpolymers, acrylic polyvinyl chloride polymers, acrylic polymers, nitrile polymers, and any other suitable anionic polymer latex polymers known in the art. The charge of the polymer lattices described above may be readily varied, as is well known in the art, by utilizing a stabilizing agent having the desired charge during preparation of the polymer latex. Specific techniques for such polymer latex systems are described in more detail in U.S. Pat. No. 6,573,212 to McCrae, et al.

The total concentration of the binder and optional co-binder may generally vary depending on the desired properties of the resulting substrate. For instance, high total binder concentrations may provide better physical properties for the coated substrate, but may likewise have an adverse affect on other properties, such as the absorptive capacity of the substrate to which it is applied. Conversely, low total binder concentrations may not provide the desired degree of durability. Thus, in most embodiments, the total amount of binder employed in the odor control coating, including the water-soluble binder and any optional co-binder, is less than about 40 wt. %, in some embodiments from about 0.5 wt. % to about 25 wt. %, and in some embodiments, from about 1 wt. % to about 15 wt. %. To enhance the drapability and odor control properties of the substrate, the water-soluble binder typically constitutes at least about 50 wt. %, in some embodiments, at least about 75 wt. %, and in some embodiments, at least about 90 wt. % of the total amount of binder employed. Conversely, when utilized, the co-binder typically constitutes less than about 50 wt. %, in some embodiments less than about 25 wt. %, and in some embodiments, less than about 10 wt. % of the total amount of binder employed.

Generally speaking, odor control coatings that contain activated carbon have a dark black color that is sometimes aesthetically displeasing to the user. To further improve the aesthetic appeal of such coatings, particles are employed in the present invention to mask, at least to some extent, the darker activated carbon particles. In this manner, the color presented to the user may be more aesthetically pleasing. Any type of particle that presents a more aesthetically pleasing color than activated carbon may be employed in the present invention. Suitable examples of inorganic masking particles that may be employed include, but are not limited to, carbonates (e.g., calcium carbonate), silicates, such as calcium silicate, alumina silicates (e.g., mica powder, clay, etc.), magnesium silicates (e.g., talc), quartzite, calcium silicate fluorite, etc.; alumina; silica; titanium dioxide; and so forth. The concentration of the particles may generally vary depending on the nature of the particles, and the desired extent of odor control and color alteration. For instance, the particles may be present in the odor control coating in an amount from about 20 wt. % to about 80 wt. %, in some embodiments from about 30 wt. % to about 70 wt. %, and in some embodiments, from about 40 wt. % to about 60 wt. %.

The present inventor has surprisingly discovered that particles having a size that is less than the size of the activated carbon particles may more effectively accomplish the desired masking function. Specifically, without intending to be limited by theory, it is believed that the small size allows for a greater number of masking particles per unit of area, which thus provides a better cumulative masking effect than would otherwise be provided by larger particles. Generally, such small masking particles have an average size of less than about 50 micrometers, in some embodiments less than about 35 micrometers, and in some embodiments, less than about 20 micrometers. For example, certain activated carbon particles have an average size of approximately 35 micrometers. In such cases, the average size of the masking particles is typically less than about 35 micrometers, and preferably much smaller, such as less than about 10 micrometers.

Although not required, the masking particles may also be porous. Without intending to be limited by theory, it is believed that porous particles may provide a passage for odorous compounds to better contact the activated carbon. For example, the particles may have pores/channels with an average diameter of greater than about 5 angstroms, in some embodiments greater than about 20 angstroms, and in some embodiments, greater than about 50 angstroms. The surface area of such particles may also be greater than about 15 square meters per gram, in some embodiments greater than about 25 square meters per gram, and in some embodiments, greater than about 50 square meters per gram. Surface area may be determined by the physical gas adsorption (B.E.T.) method of Bruanauer, Emmet, and Teller, *Journal of American Chemical Society*, Vol. 60, 1938, p. 309, with nitrogen as the adsorption gas.

In one particular embodiment, carbonate masking particles (e.g., calcium carbonate) are used to alter the black color normally associated with activated carbon odor adsorbents. The resulting color of the coating may, for example, be bluish or grayish in nature. As stated, such a color may be more aesthetically pleasing to a user, particularly when the coating is employed on substrates designed for consumer/personal use. Suitable white calcium carbonate particles that have an average particle size of about 5 micrometers are commercially available from Omya, Inc. of Proctor, Vt.

Other masking agents may also be employed in the odor control coating of the present invention to improve its aesthetic appeal. For example, the odor control coating may include a colorant, such as a pigment, dye, ink, etc. The colorant may constitute from about 0.01 to about 20 wt. %, in some embodiments from about 0.1 wt. % to about 10 wt. %, and in some embodiments, from about 0.5 wt. % to about 5 wt. % of the coating. Likewise, the colorant may be applied separately from the odor control coating to present an aesthetically appealing contrast between the color of the odor control coating and the color of the colorant. For example, the colorant may be an inorganic and/or organic pigment. Some examples of commercially available organic pigments that may be used in the present invention include those that are available from Clariant Corp. of Charlotte, N.C., under the trade designations GRAPHTOL® or CARTAREN®. Other pigments, such as lake compounds (blue lake, red lake, yellow lake, etc.), may also be employed. Inorganic and/or organic dyes may also be utilized as a colorant. Exemplary organic dye classes include triarylmethyl dyes, monoazo dyes, thiazine dyes, oxazine dyes, naphthalimide dyes, azine dyes, cyanine dyes, indigo dyes, coumarin dyes, benzimidazole dyes, paraquinoidal dyes, fluorescein dyes, diazonium salt dyes, azoic diazo dyes, phenylenediamine dyes, diazo dyes, anthraquinone dyes, trisazo dyes, xanthene dyes, proflavine dyes, sulfonaphthalein dyes, phthalocyanine dyes, carotenoid dyes, carminic acid dyes, azure dyes, acridine dyes, and so forth. One particularly suitable class of dyes includes anthraquinone compounds, which may be classified for identification by their Color Index (CI) number. For instance, some suitable anthraquinones that may be used in the present invention, as classified by their "CI" number, include Acid Black 48, Acid Blue 25 (D&C Green No. 5), Acid Blue 40, Acid Blue 41, Acid Blue 45, Acid Blue 129, Acid Green 25, Acid Green 27, Acid Green 41, Mordant Red 11 (Alizarin), Mordant Black 13 (Alizarin Blue Black B), Mordant Red 3 (Alizarin Red S), Mordant Violet 5 (Alizarin Violet 3R), Natural Red 4 (Carminic Acid), Disperse Blue 1, Disperse Blue 3, Disperse Blue 14, Natural Red 16 (Purpurin), Natural Red 8, Reactive Blue 2, and so forth. One particularly suitable colorant is available from Akzo Nobel Inks under the name "Hydrofilm 4000."

Still other compounds, such as surfactants, electrolytic salts, pH adjusters, etc., may also be included in the odor control coating of the present invention. Although not required, such additional components typically constitute less than about 5 wt. %, in some embodiments less than about 2 wt. %, and in some embodiments, from about 0.001 wt. % to about 1 wt. % of the odor control coating. For example, as is well known in the art, an electrolytic salt may be employed to control the gelation temperature of the water-soluble binder. Suitable electrolytic salts may include, but are not limited to, alkali halides or sulfates, such as sodium chloride, potassium chloride, etc.; alkaline halides or sulfates, such as calcium chloride, magnesium chloride, etc., and so forth.

As stated above, the odor control coating of the present invention is applied to a substrate. The substrate may function simply as a physical carrier for the odor control coating, or it may perform other functions of the article into which it is incorporated. To apply the odor control coating of the present invention to a substrate, the components are first typically dissolved or dispersed in a solvent to form a coating formulation. For example, one or more of the above-mentioned components may be mixed with a solvent, either sequentially or simultaneously, to form a coating formulation that may be easily applied to a substrate. Any solvent capable of dispersing or dissolving the components is suitable, for example water; alcohols such as ethanol or methanol; dimethylformamide; dimethyl sulfoxide; hydrocarbons such as pentane, butane, heptane, hexane, toluene and xylene; ethers such as diethyl ether and tetrahydrofuran; ketones and aldehydes such as acetone and methyl ethyl ketone; acids such as acetic acid and formic acid; and halogenated solvents such as dichloromethane and carbon tetrachloride; as well as mixtures thereof. The concentration of solvent in the coating formulation is generally high enough to allow easy application, handling, etc. If the amount of solvent is too large, however, the amount of activated carbon deposited on the substrate might be too low to provide the desired odor reduction. Although the actual concentration of solvent employed will generally depend on the type of activated carbon and the substrate on which it is applied, it is nonetheless typically present in an amount from about 40 wt. % to about 99 wt. %, in some embodiments from about 50 to about 95 wt. %, and in some embodiments, from about 60 wt. % to about 90 wt. % of the coating formulation.

The amount of the other components added to the coating formulation may vary depending on the amount of odor reduction desired, the wet pick-up of the application method utilized, etc. For example, activated carbon may constitute from about 0.01 wt. % to about 20 wt. %, in some embodiments from about 0.1 wt. % to about 15 wt. %, and in some embodiments, from about 0.5 wt. % to about 10 wt. % of the coating formulation. The water-soluble organic polymer may constitute from about 0.01 wt. % to about 20 wt. %, in some embodiments from about 0.1 wt. % to about 15 wt. %, and in some embodiments, from about 0.5 wt. % to about 10 wt. % of the coating formulation. Further, masking particles may constitute from about 0.1 wt. % to about 40 wt. %, in some embodiments from about 0.5 wt. % to about 30 wt. %, and in some embodiments, from about 1 wt. % to about 20 wt. %. of the coating formulation.

The solids content and/or viscosity of the coating formulation may be varied to achieve the extent of odor reduction desired. For example, the coating formulation may have a solids content of from about 1% to about 30%, in some embodiments from about 3% to about 25%, and in some embodiments, from about 5% to about 15%. By varying the solids content of the formulation, the presence of activated carbon and other components in the coating formulation may be controlled. For example, to form a coating formulation with a higher level of activated carbon, the formulation may be provided with a relatively high solids content so that a greater percentage of odor adsorbent is incorporated into the formulation during the application process. In addition, the viscosity of the coating formulation may also vary depending on the coating method and/or type of binder employed. For instance, lower viscosities may be employed for saturation coating techniques (e.g., dip-coating), while higher viscosities may be employed for drop-coating techniques. Generally, the viscosity is from about 500 to about $2 \times 10^6$ centipoise, such as measured with a Brookfield DV-1 viscometer with an LV-IV spindle. If desired, thickeners or other viscosity modifiers may be employed in the coating formulation to increase or decrease viscosity.

The coating formulation may be applied to a substrate using any conventional technique, such as bar, roll, knife, curtain, print (e.g., rotogravure), spray, slot-die, or dip-coating techniques. The materials that form the substrate (e.g., fibers) may be coated before and/or after incorporation into the substrate. The coating formulation may be applied to one or both surfaces of the substrate. For example, the odor control coating is generally present on at least the surface of the substrate that is likely to contact the targeted odor during use. In addition, the coating formulation may cover an entire surface of the substrate, or may only cover a portion of the surface. When applying the odor control coating to multiple surfaces, each surface may be coated sequentially or simultaneously.

Regardless of the manner in which the coating is applied, the resulting coated substrate may be heated to a certain temperature to drive the solvent from the coating. For example, the coated substrate may be heated to a temperature of at least about 50° C., in some embodiments at least about 70° C., and in some embodiments, at least about 80° C. By minimizing the amount of solvent in the resulting coating, a larger surface area of activated carbon may be available for contacting odorous compounds, thereby enhancing odor reduction. It should be understood, however, that relatively small amounts of solvent may still be present in the odor control coating. For example, the odor control coating may contain a solvent in an amount less than about 0.5% by weight, in some embodiments less than about 0.1% by weight, and in some embodiments, less than about 0.01% by weight.

Generally speaking, any of a variety of different substrates may be incorporated with the odor control coating of the present invention. For instance, nonwoven fabrics, woven fabrics, knit fabrics, paper web, film, foams, etc., may be applied with the odor control coating. When utilized, the nonwoven fabrics may include, but are not limited to, spunbonded webs (apertured or non-apertured), meltblown webs, bonded carded webs, air-laid webs, coform webs, hydraulically entangled webs, and so forth. Referring to FIG. 1, for example, one embodiment of a substrate 10 is shown that is in the form of a nonwoven web. Typically, the polymers used to form the substrate have a softening or melting temperature that is higher than the temperature needed to remove the solvent from the coating formulation. One or more components of such polymers may have, for instance, a softening temperature of from about 100° C. to about 400° C., in some embodiments from about 110° C. to about 300° C., and in some embodiments, from about 120° C. to about 250° C. Examples of such polymers may include, but are not limited to, synthetic polymers (e.g., polyethylene, polypropylene, polyethylene terephthalate, nylon 6, nylon 66, KEVLAR®, syndiotactic polystyrene, liquid crystalline polyesters, etc.); cellulosic polymers (softwood pulp, hardwood pulp, thermomechanical pulp, etc.); combinations thereof; and so forth.

The solids add-on level of the odor control coating may also be varied as desired. The "solids add-on level" is determined by subtracting the weight of the untreated substrate from the weight of the treated substrate (after drying), dividing this calculated weight by the weight of the untreated substrate, and then multiplying by 100%. One particular benefit of the present invention is that high solids add-on levels, and consequently high levels of odor control, may be achieved without a substantial sacrifice in durability of the coating. In some embodiments, for example, the add-on level is at least about 20% to about 600%, in some embodiments from about 60% to about 500%, and in some embodiments, from about 100% to about 400%. The thickness of the odor control coating may also vary. For example, the thickness may range from about 0.001 millimeters to about 0.4 millimeters, in some embodiments, from about 0.01 millimeters to about 0.30 millimeters, and in some embodiments, from about 0.01 millimeters to about 0.20 millimeters. Such a relatively thin coating may enhance the flexibility of the substrate, while still providing uniform heating.

To maintain absorbency, porosity, flexibility, and/or some other characteristic of the substrate, it may sometimes be desired to apply the odor control coating so as to cover less than 100%, in some embodiments from about 10% to about 80%, and in some embodiments, from about 20% to about 60% of the area of one or more surfaces of the substrate. For instance, in one particular embodiment, the odor control coating is applied to the substrate in a preselected pattern (e.g., reticular pattern, diamond-shaped grid, dots, and so forth). Although not required, such a patterned odor control coating may provide sufficient odor control without covering a substantial portion of the surface area of the substrate. This may be desired to optimize flexibility, absorbency, or other characteristics of the substrate. It should be understood, however, that the coating may also be applied uniformly to one or more surfaces of the substrate. In addition, a patterned odor control coating may also provide different functionality to each zone. For example, in one embodiment, the substrate is treated with two or more patterns of coated regions that may or may not overlap. The regions may be on the same or different surfaces of the substrate. In one embodiment, one region of a substrate is coated with a first odor control coating, while another region is coated with a second odor control coating. Likewise, an article may contain a first coated substrate and a second coated substrate. In either case, one region or substrate may be configured to reduce one type of odor, while another region or substrate may be configured to reduce another type of odor. Alternatively, one region or substrate may possess a higher level of an odor control coating than another region or substrate to provide different levels of odor reduction.

Figure 2:
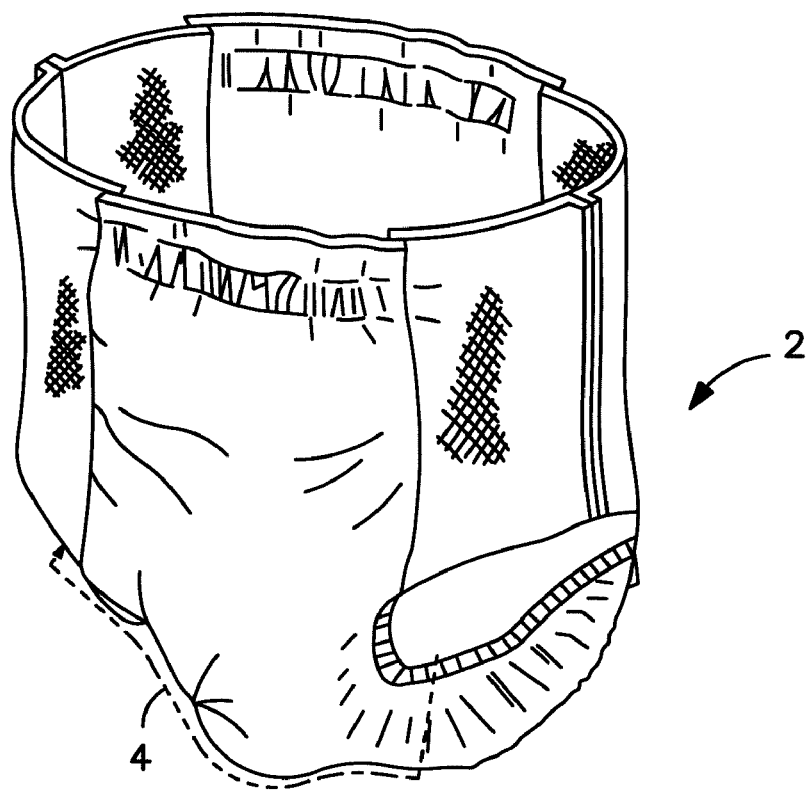
FIG. 2 illustrates a perspective view of an absorbent article that may be formed according to one embodiment of the present invention.

The odor control coating of the present invention may be employed in a wide range of articles. If desired, the odor control coating may be used in one or more components of an absorbent article, such as in a liquid-permeable layer (e.g., bodyside liner, surge layer, etc.), a substantially liquid-impermeable layer, a breathable layer (e.g., outer cover, ventilation layer, baffle, etc.), absorbent core, elastic member, and so forth. Several examples of such absorbent articles are described in U.S. Pat. Nos. 5,197,959 to Buell; 5,085,654 to Buell; 5,634,916 to Lavon, et al.; 5,569,234 to Buell, et al.; 5,716,349 to Taylor, et al.; 4,950,264 to Osborn, III; 5,009,653 to Osborn, III; 5,509,914 to Osborn, III; 5,649,916 to DiPalma, et al.; 5,267,992 to Van Tillburg; 4,687,478 to Van Tillburg; 4,285,343 to McNair; 4,608,047 to Mattingly; 5,342,342 to Kitaoka; 5,190,563 to Herron, et al.; 5,702,378 to Widlund, et al.; 5,308,346 to Sneller, et al.; 6,110,158 to Kielpikowski; 6,663,611 to Blaney, et al.; and WO 99/00093 to Patterson, et al., which are incorporated herein in their entirety by reference thereto for all purposes. Referring to FIG. 2, for example, an absorbent article 2 is shown that has a pant-like configuration useful for diapers, child training pants, child swim wear, adult incontinence articles, and so forth. The article 2 includes a chassis 4 containing multiple layers including, for instance, a liquid-permeable top layer, an absorbent core layer and a breathable liquid-impermeable outer cover layer that faces away from the wearer.

The odor control coating of the present invention is versatile and may also be used with other types of articles of manufacture. For instance, the odor control coating may be used in air filters, such as house filters, vent filters, disposable facemasks, and facemask filters. Exemplary facemasks, for instance, are described and shown, for example, in U.S. Pat. Nos. 4,802,473; 4,969,457; 5,322,061; 5,383,450; 5,553,608; 5,020,533; 5,813,398; and 6,427,693, which are incorporated herein in their entirety by reference thereto for all purposes. In one embodiment, a substrate coated with the odor control coating of the present invention may be utilized as a filtration layer of the facemask. Filtration layers, such as meltblown nonwoven webs, spunbond nonwoven webs, and laminates thereof, are well known in the art.

In still other embodiments, the odor control coating may be employed in conjunction with a garment. For instance, garments, such as meat and seafood packing industry aprons/attire, grocery store aprons, paper mill aprons/attire, farm/dairy garments, hunting garments, etc., may be incorporated with the odor control coating of the present invention. As an example, hunters often wear garments that are camouflaged for the particular hunting environment. The odor control coating of the present invention may thus be used to form the camouflage pattern. Specifically, the odor control coating may impart the desired color pattern and also help reduce human odor during hunting.

The effectiveness of the odor control coating of the present invention may be measured in a variety of ways. For example, the percent of an odorous compound adsorbed by the odor control coating may be determined using the headspace gas chromatography test as set forth herein. In some embodiments, for instance, the odor control coating of the present invention is capable of adsorbing at least about 25%, in some embodiments at least about 45%, and in some embodiments, at least about 65% of a particular odorous compound. The effectiveness of the odor control coating in removing odors may also be measured in terms of "Relative Adsorption Efficiency", which is also determined using headspace gas chromatography and measured in terms of milligrams of odor adsorbed per gram of the odor control coating. It should be recognized that the surface chemistry of any one type of odor control coating may not be suitable to reduce all types of odors, and that low adsorption of one or more odorous compounds may be compensated by good adsorption of other odorous compounds.

The present invention may be better understood with reference to the following examples.

Test Methods

Quantitative odor adsorption was determined using a test known as "Headspace Gas Chromatography." Headspace gas chromatography testing was conducted on an Agilent Technologies 5890, Series II gas chromatograph with an Agilent Technology 7694 headspace sampler (Agilent Technologies, Waldbronn, Germany). Helium was used as the carrier gas (injection port pressure: 12.7 psig; headspace vial pressure: 15.8 psig; supply line pressure is at 60 psig). A DB-624 column was used for the odorous compound that had a length of 30 meters and an internal diameter of 0.25 millimeters. Such a column is available from J&W Scientific, Inc. of Folsom, Calif.

The operating parameters used for the headspace gas chromatography are shown below in Table 1:

TABLE 1

| Operating Parameters for the Headspace Gas Chromatography Device Headspace Parameters | | |
|---|---|---|
| Zone Temps, ° C. | Oven | 37 |
| | Loop | 85 |
| | Transfer Line | 90 |
| Event Time, minutes | GC Cycle time | 10.0 |
| | Vial eq. Time | 10.0 |
| | Pressuriz. Time | 0.20 |
| | Loop fill time | 0.20 |
| | Loop eq. Time | 0.15 |
| | Inject time | 0.30 |
| Vial Parameters | First vial | 1 |
| | Last vial | 1 |
| | Shake | [off] |

The test procedure involved placing 0.0075 to 0.0120 gram of fabric, depending on the level of carbon coating, in a 20-cubic centimeter headspace vial. Using a syringe, an aliquot of an odorous compound was also placed in the vial. Specifically, testing was done with 2 microliters of pyridine. The vial was then sealed with a cap and a septum and placed in the headspace gas chromatography oven at 37° C. After ten minutes, a hollow needle was inserted through the septum and into the vial. A 1-cubic centimeter sample of the headspace (air inside the vial) was then injected into the gas chromatograph. Initially, a control vial with only the aliquot of odorous compound was tested to define 0% odorous compound adsorption. To calculate the amount of headspace odorous compound removed by the sample, the peak area for the odorous compound from the vial with the sample was compared to the peak area from the odorous compound control vial.

EXAMPLE 1

The ability to form an odor control substrate in accordance with the present invention was demonstrated. Initially, a bonded carded web fabric was provided that had a size of 7" by 12" and a basis weight of 0.9 ounces per square yard. The fabric was formed from a blend of 75 wt. % bicomponent fibers and 25 wt. % polyester fibers. The bicomponent fibers were obtained from Fibervisions, Inc. of Covington, Ga. under the name "ESC 215", which had a polyethylene sheath and polypropylene core, a denier of 3.0, and 0.55 wt. % "HR6" finish. The polyester fibers were obtained from Invista of Wichita, Kans. under the name "T-295", which had a denier of 6.0 and contained a 0.5 wt. % L1 finish.

The coating formulation was prepared as follows. In a 400-milliliter pyrex beaker, 5.0 grams of "Metolose SM4000" (methyl cellulose, available from Shin-Etsu Chemical Co., Ltd.) and 12.5 grams of sodium chloride (Mallinckrodt) were added to 150.1 grams of warm (ca. 70° C.) distilled water while stirring over a hot plate. After about 5 minutes, the hot plate was removed to allow the stirring liquid to cool. Thereafter, 100.1 grams of an aqueous slurry of calcium carbonate particles was added to the formulation while stirring. The aqueous calcium carbonate slurry was obtained from Omya, Inc. under the name "XC4900" and had a solids content of 40.8%. 10.0 grams of activated carbon powder was then added to the formulation. The activated carbon was made by MeadWestvaco Corp. under the name "Nuchar SA-20." After the carbon addition, the formulation changed color from a bright white to a light black.

The beaker was then placed in an ice bath to cool the formulation and increase its viscosity. The viscosity was observed to increase dramatically when the temperature of the formulation reached about 17° C. The ice bath was then removed and the formulation was manually stirred with a spatula as it warmed up to about room temperature. The percent solids of the formulation was determined to be 25.0%. The calculated concentration of each component of the aqueous formulation is also set forth below in Table 2.

TABLE 2

Components of the Aqueous Formulation

| Component | Calculated Amount |
|---|---|
| Activated Carbon | 3.6% |
| Binder | 1.8% |
| Calcium Carbonate | 14.7% |
| Sodium Chloride | 4.5% |
| Water | 75.4% |

One side of the fabric was coated with the formulation using a #60 single wound metering rod. After applying the aqueous formulation, the coated fabric was dried in a forced air oven at 110° C. for 10 to 15 minutes. The concentration of the components of the coating was then calculated from the initial fabric weight (1.9 grams), the dry coated fabric weight (6.7 grams), and the composition of the aqueous formulation. The results are set forth below in Table 3.

TABLE 3

Components of the Coating

| Component | Calculated Amount |
|---|---|
| Activated Carbon | 14.6% |
| Binder | 7.4% |
| Calcium Carbonate | 59.7% |
| Sodium Chloride | 18.3% |
| Solids Add-On Level | ~253% |

The fabric was observed to have a medium gray color and good drape characteristics, despite the high add-on level of particles. Further, using the Headspace Gas Chromatography test described above, the fabric was determined to remove 83 milligrams of pyridine per gram of the fabric.

EXAMPLE 2

The ability to form an odor control substrate in accordance with the present invention was demonstrated. The coating formulation was prepared as follows. In a 400-milliliter pyrex beaker, 5.0 grams of "Metolose SM4000" (methyl cellulose, available from Shin-Etsu Chemical Co., Ltd.) were added to 149.3 grams of warm (ca. 70° C.) distilled water while stirring over a hot plate. After about 5 minutes, the hot plate was removed to allow the stirring liquid to cool. Thereafter, 74.3 grams of an aqueous slurry of calcium carbonate particles was added to the formulation while stirring. The aqueous calcium carbonate slurry was obtained from Omya, Inc. under the name "XC4900" and had a solids content of 27.7%. 12.0 grams of activated carbon powder was then added to the formulation. The activated carbon was made by MeadWestvaco Corp. under the name "Nuchar SA-1500." After the carbon addition, the formulation changed color from a bright white to a light black. The formulation was allowed to cool for several hours.

The beaker was then placed in an ice bath to cool the formulation and increase its viscosity. The viscosity was observed to increase dramatically when the temperature of the formulation reached about 17° C. The ice bath was then removed and the formulation was manually stirred with a spatula as it warmed up to about room temperature. The percent solids of the formulation was determined to be 15.5%. The calculated concentration of each component of the aqueous formulation is also set forth below in Table 4.

TABLE 4

Components of the Aqueous Formulation

| Component | Calculated Amount |
|---|---|
| Activated Carbon | 5.0% |
| Binder | 2.1% |
| Calcium Carbonate | 8.6% |
| Water | 84.3% |

One side of a bonded carded fabric, such as described in Example 1, was then coated with the formulation using a #60 single wound metering rod. After applying the aqueous formulation, the coated fabric was dried in a forced air oven at 110° C. for about 15 minutes. The concentration of the components of the coating was then calculated from the initial fabric weight (1.9 grams), the dry coated fabric weight (4.4 grams), and the composition of the aqueous formulation. The results are set forth below in Table 5.

TABLE 5

Components of the Coating

| Component | Calculated Amount |
|---|---|
| Activated Carbon | 32.0% |
| Binder | 13.4% |
| Calcium Carbonate | 54.6% |
| Solids Add-On Level | ~132% |

The fabric was observed to have a medium gray color and good drape characteristics, despite the high add-on level of particles. Further, using the Headspace Gas Chromatography test described above, the fabric was determined to remove 139 milligrams of pyridine per gram of the fabric.

EXAMPLE 3

The ability to form an odor control substrate in accordance with the present invention was demonstrated. The coating formulation was prepared as follows. In a 400-milliliter pyrex beaker, 5.0 grams of "Bermocoll E230 FQ" (an ethyl hydroxyethyl cellulose available from Akzo Nobel) were added to 150.0 grams of warm (ca. 70° C.) distilled water while stirring over a hot plate. After about 5 minutes, the hot plate was removed to allow the stirring liquid to cool. When the solution was cool (ca. 23° C.) and noticeably more clear and viscous, the percent solids was measured at 2.9%. Thereafter, 75.7 grams of an aqueous slurry of calcium carbonate particles was added to the formulation while stirring. The aqueous calcium carbonate slurry was obtained from Omya, Inc. under the name "XC4900" and had a solids content of 27.6%. 12.0 grams of activated carbon powder was then added to the formulation. The activated carbon was made by MeadWestvaco Corp. under the name "Nuchar SA-20." This final formulation was stirred for about 30 minutes and then the viscosity and percent solids were measured. The viscosity was 3930 centipoise (Brookfield Model DV-I viscometer with an LV-2 spindle at 1.0 rpm) and the percent solids was 15.4%. The calculated concentration of each component of the aqueous formulation is also set forth below in Table 6.

TABLE 6

Components of the Aqueous Formulation

| Component | Calculated Amount |
|---|---|
| Activated Carbon | 4.9% |
| Binder | 2.1% |
| Calcium Carbonate | 8.6% |
| Water | 84.4% |

One side of a bonded carded fabric, such as described in Example 1, was then coated with the formulation using a #60 single wound metering rod. After applying the aqueous formulation, the coated fabric was dried in a forced air oven at 110° C. for about 15 minutes. The concentration of the components of the coating was then calculated from the initial fabric weight (1.9 grams), the dry coated fabric weight (4.8 grams), and the composition of the aqueous formulation. The results are set forth below in Table 7.

TABLE 7

Components of the Coating

| Component | Calculated Amount |
|---|---|
| Activated Carbon | 31.4% |
| Binder | 13.3% |
| Calcium Carbonate | 55.2% |
| Solids Add-On Level | ~153% |

The fabric was observed to have a medium gray color and good drape characteristics, despite the high add-on level of particles. Further, using the Headspace Gas Chromatography test described above, the fabric was determined to remove 115 milligrams of pyridine per gram of the fabric.

EXAMPLE 4

The ability to form an odor control substrate in accordance with the present invention was demonstrated. The coating formulation was prepared as follows. In a 400-milliliter pyrex beaker, 3.0 grams of "Bermocoll E230 FQ" (ethyl hydroxyethyl cellulose, available from Akzo Nobel) was added to 201.3 grams of warm (ca. 70° C.) distilled water while stirring over a hot plate. After about 5 minutes, the hot plate was removed to allow the stirring liquid to cool. When the solution had cooled (ca. 23° C.), the percent solids were measured at 1.1%. The viscosity was also measured at 76.5 centipoise using a Brookfield Model DV-I viscometer with LV-2 spindle at 60 RPM. Thereafter, 36.3 grams of an aqueous slurry of calcium carbonate particles was added to the formulation while stirring. The aqueous calcium carbonate slurry was obtained from Omya, Inc. under the name "XC4900" and had a solids content of 27.4%. 4.5 grams of activated carbon powder was then added to the formulation. The activated carbon was made by MeadWestvaco Corp. under the name "Nuchar SA-20."

After stirring these components for about 15 minutes, the viscosity was again measured using the same settings described above. The value was only 101.5 centipoise, considered too low for the rod coating method. Therefore, the formulation was warmed to about 70° C. and an additional 2.0 grams of the Bermocoll E230 FQ was added. After cooling this final formulation to about room temperature with an ice bath while stirring, the viscosity was measured at 635 centipoise (same setting as above, but with a spindle RPM of 12). The percent solids were also measured at 7.95%. The calculated concentration of each component of the aqueous formulation is also set forth below in Table 8.

TABLE 8

Components of the Aqueous Formulation

| Component | Calculated Amount |
|---|---|
| Activated Carbon | 1.8% |
| Binder | 2.0% |
| Calcium Carbonate | 4.0% |
| Water | 92.2% |

One side of the fabric described in Example 1 was then coated with the formulation using a #60 single wound metering rod. In addition, a 5.5"×12.0" piece of polypropylene spunbond fabric (basis weight of 0.55 ounces per square yard) was also coated with the formulation using a #60 single wound metering rod. After applying the aqueous formulation, the coated fabric was dried in a forced air oven at 110° C. for 10 to 15 minutes. The concentration of the components of the coating was then calculated from the initial fabric weight (1.8 grams for the bonded carded web, 0.8 grams for the spunbond web), the dry coated fabric weight (3.3 grams for the bonded carded web, 1.2 grams for the spunbond web), and the composition of the aqueous formulation. The results are set forth below in Tables 9 and 10.

TABLE 9

Components of the Coating for the Bonded Carded Web

| Component | Calculated Amount |
|---|---|
| Activated Carbon | 23.2% |
| Binder | 51.1% |
| Calcium Carbonate | 25.7% |
| Solids Add-On Level | ~83% |

TABLE 10

Components of the Coating for the Spunbond Web

| Component | Calculated Amount |
|---|---|
| Activated Carbon | 23.2% |
| Binder | 25.7% |
| Calcium Carbonate | 51.1% |
| Solids Add-On Level | ~50% |

The fabrics were observed to have a medium gray color and good drape characteristics, despite the high add-on level of particles. Further, using the Headspace Gas Chromatography test described above, the bonded carded fabric was determined to remove 78 milligrams of pyridine per gram of the fabric.

EXAMPLE 5

The ability to form an odor control substrate in accordance with the present invention was demonstrated. The coating formulation was prepared as follows. In a 400-milliliter pyrex beaker, 5.0 grams of "Bermocoll E230 FQ" (ethyl hydroxyethyl cellulose, available from Akzo Nobel) was added to 204.7 grams of warm (ca. 70° C.) distilled water while stirring over a hot plate. After about 5 minutes, the hot plate was removed to allow the stirring liquid to cool. When the solution had cooled (ca. 26° C.), the percent solids were measured at 2.2%. The viscosity was also measured at 397 centipoise using a Brookfield Model DV-I viscometer with LV-2 spindle at 30 RPM. Thereafter, 41.6 grams of an aqueous slurry of calcium carbonate particles was added to the formulation while stirring. The aqueous calcium carbonate slurry was obtained from Omya, Inc. under the name "XC4900" and had a solids content of 27.9%. 4.8 grams of activated carbon powder was then added to the formulation. The activated carbon was made by MeadWestvaco Corp. under the name "Nuchar SA-20." In addition, 21.2 grams of "Hydrofilm 4000", a water-based flexographic ink (cyan) available from Akzo Nobel Inks was also added to the formulation. The percent solids was 43.4%.

After stirring these components for about 30 minutes, the viscosity was again measured using the same settings described above. The viscosity was 555 centipoise and the solids content was 10.75%. The calculated concentration of each component of the aqueous formulation is also set forth below in Table 11.

TABLE 11

Components of the Aqueous Formulation

| Component | Calculated Amount |
| --- | --- |
| Activated Carbon | 1.7% |
| Binder | 1.8% |
| Calcium Carbonate | 4.2% |
| Cyan Ink | 3.3% |
| Water | 89.0% |

One side of the fabric described in Example 1 was then coated with the formulation using a #60 single wound metering rod. After applying the aqueous formulation, the coated fabric was dried overnight in a forced air oven at 90° C. The concentration of the components of the coating was then calculated from the initial fabric weight (2.1 grams), the dry coated fabric weight (4.0 grams), and the composition of the aqueous formulation. The results are set forth below in Table 12.

TABLE 12

Components of the Coating

| Component | Calculated Amount |
| --- | --- |
| Activated Carbon | 15.7% |
| Binder | 16.4% |
| Calcium Carbonate | 37.8% |
| Cyan Ink | 30.1% |
| Solids Add-On Level | ~90% |

The fabric was observed to have a bright, dark blue color, similar to that of the cyan ink. Further, using the Headspace Gas Chromatography test described above, the bonded carded fabric was determined to remove 76 milligrams of pyridine per gram of the fabric.

EXAMPLE 6

The ability to form an odor control substrate in accordance with the present invention was demonstrated. The coating formulation was prepared as follows. In a 400-milliliter pyrex beaker, 5.0 grams of "Bermocoll E230 FQ" (ethyl hydroxyethyl cellulose, available from Akzo Nobel) was added to 202.1 grams of warm (ca. 70° C.) distilled water while stirring over a hot plate. After about 5 minutes, the hot plate was removed to allow the stirring liquid to cool. When the solution had cooled (ca. 22° C.), 37.1 grams of an aqueous slurry of calcium carbonate particles was added to the formulation while stirring. The aqueous calcium carbonate slurry was obtained from Omya, Inc. under the name "XC4900" and had a solids content of 27.9%. 4.8 grams of activated carbon powder was then added to the formulation. The activated carbon was made by MeadWestvaco Corp. under the name "Nuchar SA-20." In addition, 3.4 grams of "Hydrofilm 4000", a water-based flexographic ink (cyan) available from Akzo Nobel Inks was also added to the formulation. After stirring these components for about 15 minutes, the viscosity was measured using the same settings described in Example 5. The viscosity was 574 centipoise and the solids content was 8.57%. The calculated concentration of each component of the aqueous formulation is also set forth below in Table 13.

TABLE 13

Components of the Aqueous Formulation

| Component | Calculated Amount |
| --- | --- |
| Activated Carbon | 1.9% |
| Binder | 2.0% |
| Calcium Carbonate | 4.1% |
| Cyan Ink | 0.6% |
| Water | 91.4% |

One side of the fabric described in Example 1 was then coated with the formulation using a #60 single wound metering rod. After applying the aqueous formulation, the coated fabric was dried in a forced air oven at 110° C. for 15 to 20 minutes. The concentration of the components of the coating was then calculated from the initial fabric weight (2.0 grams), the dry coated fabric weight (3.5 grams), and the composition of the aqueous formulation. The results are set forth below in Table 14.

TABLE 14

Components of the Coating

| Component | Calculated Amount |
| --- | --- |
| Activated Carbon | 22.1% |
| Binder | 23.1% |
| Calcium Carbonate | 47.8% |
| Cyan Ink | 7.0% |
| Solids Add-On Level | ~75% |

The fabric was observed to have a light blue color. Further, using the Headspace Gas Chromatography test described above, the bonded carded fabric was determined to remove 75 milligrams of pyridine per gram of the fabric.

EXAMPLE 7

The ability to form an odor control substrate in accordance with the present invention was demonstrated. The coating formulation was prepared as follows. In a 400-milliliter pyrex beaker, 170.5 grams of an aqueous slurry of calcium carbonate particles was added to 151.7 grams of an activated carbon ink while stirring. The aqueous calcium carbonate slurry was obtained from Omya, Inc. under the name "XC4900" and had a solids content of 27.8%. The activated carbon ink was made by MeadWestvaco Corp of Stamford, Conn. under the name "DPX-8433-68B", which contained 12 to 16 wt. % activated carbon, 20 to 24 wt. % styrene acrylic binder, and 62 to 66 wt. % water. After about 30 minutes of stirring, the viscosity of the formulation was measured at 100.0 centipoise (LV-2 spindle at 60 RPM) and the percent solids was 30.6%.

Thereafter, 191.5 grams of the above-described formulation was placed into a 250-milliliter pyrex beaker and heated to about 63° C. while stirring. 3.8 grams of "Bermocoll E230 FQ" (ethyl hydroxyethyl cellulose, available from Akzo Nobel) was added and the formulation became noticeably more viscous, particularly after the hot plate was removed and the formulation was cooled to room temperature in cold water. The percent solids were measured at 32.8%. The viscosity was also measured at 1,700,000 centipoise using a Brookfield Model DV-I viscometer with LV-4 spindle at 0.3 RPM. The calculated concentration of each component of the aqueous formulation is also set forth below in Table 15.

TABLE 15

Components of the Aqueous Formulation

| Component | Calculated Amount |
| --- | --- |
| Activated Carbon | 6.5% |
| E230 FQ | 2.0% |
| Latex | 10.2% |
| Calcium Carbonate | 14.4% |
| Water | 66.9% |

One side of the fabric described in Example 1 was then coated with the formulation using a #60 single wound metering rod. After applying the aqueous formulation, the coated fabric was dried for 20 minutes in a forced air oven at 110° C. The concentration of the components of the coating was then calculated from the initial fabric weight (2.0 grams), the dry coated fabric weight (6.3 grams), and the composition of the aqueous formulation. The results are set forth below in Table 16.

TABLE 16

Components of the Coating

| Component | Calculated Amount |
| --- | --- |
| Activated Carbon | 19.6% |
| E230 FQ | 6.0% |
| Latex | 30.8% |
| Calcium Carbonate | 43.6% |
| Solids Add-On Level | ~215% |

The fabric was observed to have a charcoal black color. Further, using the Headspace Gas Chromatography test described above, the bonded carded fabric was determined to remove 71 milligrams of pyridine per gram of the fabric.

EXAMPLE 8

A coating formulation was prepared for comparative purposes that contained an activated carbon ink made by Mead-Westvaco Corp of Stamford, Conn. under the name "DPX-8433-68B" that was diluted 50/50 with distilled water. The resulting formulation thus contained 6 to 8 wt. % activated carbon, 10 to 12 wt. % styrene acrylic binder, and 81 to 83 wt. % water. The percent solids of the activated carbon formulation was 16.0%. A 7-inch wide, 200-yard roll of a bonded carded fabric, such as described in Example 1, was then coated with the formulation at a rate of about 17 feet per minute. The fabric was saturated with the formulation by applying it to the top side from a plastic tube "shower" and to the bottom side by an applicator roll that picked up the formulation from a metal pan. The saturated fabric was nipped at a pressure of 90 psig and then dried over four steam cans (measured temperatures of 115.6° C., 115° C., 117.8° C., and 114.4° C.). The concentration of the components of the coating was then calculated from a 7"×18" piece of the untreated fabric (2.91 grams), the dry coated fabric weight (4.39 grams), and the composition of the aqueous formulation. The results are set forth below in Table 17.

TABLE 17

Components of the Coating

| Component | Calculated Amount |
| --- | --- |
| Activated Carbon | 38.9% |
| Binder | 61.1% |
| Solids Add-On Level | ~50.9% |

The fabric was observed to have a charcoal black color and was stiff, most likely due to the high level of binder present in the activated carbon coating. The fabric also had an odor, which was most likely a residual from the binder present in the DPX-8433-68B activated carbon ink. Further, using the Headspace Gas Chromatography test described above, the fabric was determined to remove 81 milligrams of pyridine per gram of the fabric.

EXAMPLE 9

A coating formulation was prepared for comparative purposes that contained an activated carbon ink made by Mead-Westvaco Corp of Stamford, Conn. under the name "DPX-8433-68B", which contained 12 to 16 wt. % activated carbon, 20 to 24 wt. % styrene acrylic binder, and 62 to 66 wt % water. The percent solids of the activated carbon formulation was 34.8%. The fabric described in Example 1 was saturated with the formulation by applying it to the top side from a plastic funnel and to the bottom side by an applicator roll that picked up the ink from a metal pan. The saturated fabric was run through a nip and then dried over a stationary steam can. The concentration of the components of the coating was then calculated from the untreated fabric weight (1.7 grams), the dry coated fabric weight (4.1 grams), and the composition of the aqueous formulation. The results are set forth below in Table 18.

TABLE 18

Components of the Coating

| Component | Calculated Amount |
| --- | --- |
| Activated Carbon | 38.9% |
| Binder | 61.1% |
| Solids Add-On Level | ~141% |

The fabric was observed to have a charcoal black color and was stiff, most likely due to the high level of binder present in the activated carbon coating. The fabric also had an odor, which was most likely a residual from the binder present in the DPX-8433-68B activated carbon ink. Further, using the Headspace Gas Chromatography test described above, the fabric was determined to remove 110 milligrams of pyridine per gram of the fabric.

EXAMPLE 10

A coating formulation was prepared for comparative purposes. Specifically, the formulation was prepared as follows. In a 400-milliliter pyrex beaker, 170.5 grams of an aqueous slurry of calcium carbonate particles was added to 151.7 grams of an activated carbon ink while stirring. The aqueous calcium carbonate slurry was obtained from Omya, Inc. under the name "XC4900" and had a solids content of 27.8%. The activated carbon ink was made by MeadWestvaco Corp of Stamford, Conn. under the name "DPX-8433-68B", which contained 12 to 16 wt. % activated carbon, 20 to 24 wt. % styrene acrylic binder, and 62 to 66 wt. % water. After about 30 minutes of stirring, the viscosity of the formulation was measured at 100.0 centipoise (LV-2 spindle at 60 RPM) and the percent solids was 30.6%. The resulting formulation was then coated onto one side of the fabric described in Example 1 using a #60 single wound metering rod. However, due to the low viscosity, the formulation essentially saturated the fabric throughout instead of being confined mostly to the coated side. The calculated concentration of each component of the aqueous formulation is also set forth below in Table 19.

TABLE 19

Components of the Aqueous Formulation

| Component | Calculated Amount |
| --- | --- |
| Activated Carbon | 6.6% |
| Binder | 10.4% |
| Calcium Carbonate | 14.7% |
| Water | 68.3% |

The concentration of the components of the coating was then calculated from the untreated fabric weight (2.1 grams), the dry coated fabric weight (9.1 grams), and the composition of the aqueous formulation. The results are set forth below in Table 20.

TABLE 20

Components of the Coating

| Component | Calculated Amount |
| --- | --- |
| Activated Carbon | 20.8% |
| Binder | 46.4% |
| Calcium Carbonate | 32.8% |
| Solids Add-On Level | ~333% |

The fabric was observed to have a charcoal black color, instead of the gray color that might be expected when using white calcium carbonate particles. Further, using the Headspace Gas Chromatography test described above, the fabric was determined to remove 86 milligrams of pyridine per gram of the fabric.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A substrate that contains an odor control coating, the odor control coating comprising activated carbon, a binder, and a masking agent, wherein the binder comprises a water-soluble organic polymer and a polymer latex, wherein the polymer latex is sufficiently crosslinked to be substantially insoluble in water, and further wherein the masking agent comprises inorganic particles having an average size less than about 35 micrometers and the average size of the inorganic particles is less than the average size of the activated carbon.

2. The substrate of claim 1, wherein the activated carbon comprises from about 1 wt. % to about 50 wt. % of the odor control coating.

3. The substrate of claim 1, wherein the activated carbon comprises from about 5 wt. % to about 20 wt. % of the odor control coating.

4. The substrate of claim 1, wherein the binder comprises less than about 40 wt. % of the odor control coating.

5. The substrate of claim 1, wherein the binder comprises from about 0.5 wt. % to about 25 wt. % of the odor control coating.

6. The substrate of claim 1, wherein the water-soluble organic polymer constitutes at least about 50 wt. % of the binder.

7. The substrate of claim 1, wherein the water-soluble organic polymer constitutes at least about 90 wt. % of the binder.

8. The substrate of claim 1, wherein the polymer latex constitutes less than about 50 wt. % of the binder.

9. The substrate of claim 1, wherein the polymer latex constitutes less than about 25 wt. % of the binder.

10. The substrate of claim 1, wherein the water-soluble organic polymer includes a nonionic cellulosic ether.

11. The substrate of claim 10, wherein the nonionic cellulosic ether is selected from the group consisting of alkyl cellulose ethers, hydroxyalkyl cellulose ethers, alkyl hydroxyalkyl cellulose ethers, and combinations thereof.

12. The substrate of claim 1, wherein the polymer latex is selected from the group consisting of styrene-butadiene copolymers, polyvinyl acetate homopolymers, vinyl-acetate ethylene copolymers, vinyl-acetate acrylic copolymers, ethylene-vinyl chloride copolymers, ethylene-vinyl chloride-vinyl acetate terpolymers, acrylic polyvinyl chloride polymers, acrylic polymers, nitrile polymers, and combinations thereof.

13. The substrate of claim 1, wherein the inorganic particles comprise from about 20 wt. % to about 80 wt. % of the odor control coating.

14. The substrate of claim 1, wherein the inorganic particles are calcium carbonate particles.

15. The substrate of claim 1, wherein the solids add-on level is from about 20% to about 600%.

16. The substrate of claim 1, wherein the odor control coating comprises a colorant.

17. The substrate of claim 1, wherein the substrate contains a nonwoven web.

18. An absorbent article that comprises a substrate, wherein the substrate contains an odor control coating that comprises activated carbon, a binder, and a masking agent, wherein the binder comprises a water-soluble organic polymer and a polymer latex, wherein the polymer latex is sufficiently crosslinked to be substantially insoluble in water, and further wherein the masking agent comprises inorganic particles having an average size less than about 35 micrometers and the average size of the inorganic particles is less than the average size of the activated carbon.

19. The absorbent article of claim 18, wherein the activated carbon comprises from about 1 wt. % to about 50 wt. % of the odor control coating.

20. The absorbent article of claim 18, wherein the activated carbon comprises from about 5 wt. % to about 20 wt. % of the odor control coating.

21. The absorbent article of claim 18, wherein the binder comprises less than about 40 wt. % of the odor control coating.

22. The absorbent article of claim 18, wherein the binder comprises from about 0.5 wt. % to about 25 wt. % of the odor control coating.

23. The absorbent article of claim 18, wherein the water-soluble organic polymer constitutes at least about 50 wt. % of the binder and the polymer latex constitutes less than about 50 wt. % of the binder.

24. The absorbent article of claim 18, wherein the water-soluble organic polymer includes a nonionic cellulosic ether.

25. The absorbent article of claim 18, wherein the polymer latex is selected from the group consisting of styrene-butadiene copolymers, polyvinyl acetate homopolymers, vinyl-acetate ethylene copolymers, vinyl-acetate acrylic copolymers, ethylene-vinyl chloride copolymers, ethylene-vinyl chloride-vinyl acetate terpolymers, acrylic polyvinyl chloride polymers, acrylic polymers, nitrile polymers, and combinations thereof.

26. The absorbent article of claim 18, wherein the inorganic particles comprise from about 20 wt. % to about 80 wt. % of the odor control coating.

27. The absorbent article of claim 18, wherein the inorganic particles are calcium carbonate particles.

28. The absorbent article of claim 18, wherein the solids add-on level is from about 20% to about 600%.

29. The absorbent article of claim 18, wherein the odor control coating comprises a colorant.

30. The absorbent article of claim 18, wherein the substrate contains a nonwoven web.

31. The absorbent article of claim 18, wherein the absorbent article contains a liquid-permeable layer and a liquid-impermeable layer.

32. The absorbent article of claim 31, wherein the liquid-permeable layer contains the substrate.

33. The absorbent article of claim 31, wherein the liquid-impermeable layer contains the substrate.

34. The absorbent article of claim 18, wherein the article is a diaper.

\* \* \* \* \*